(12) United States Patent
Jau et al.

(10) Patent No.: US 8,088,960 B2
(45) Date of Patent: Jan. 3, 2012

(54) PROCESS FOR THE PRODUCTION OF SUBSTITUTED BROMOBENZENES

(75) Inventors: Beat Jau, Muenchwilen (CH); Colin Ellis, Hull (GB); Linhua Wang, Huddersfield (GB)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 12/446,793

(22) PCT Filed: Oct. 8, 2007

(86) PCT No.: PCT/EP2007/008697
§ 371 (c)(1),
(2), (4) Date: Dec. 6, 2010

(87) PCT Pub. No.: WO2008/049507
PCT Pub. Date: May 2, 2008

(65) Prior Publication Data
US 2011/0065968 A1 Mar. 17, 2011

Related U.S. Application Data

(63) Continuation-in-part of application No. PCT/EP2007/008697, filed on Oct. 8, 2007.

(30) Foreign Application Priority Data

Oct. 25, 2006 (EP) .................... 06022279

(51) Int. Cl.
C07C 17/00 (2006.01)
C07C 22/00 (2006.01)
(52) U.S. Cl. ...................... 570/206; 570/143
(58) Field of Classification Search .......... 570/143, 570/206
See application file for complete search history.

(56) References Cited

FOREIGN PATENT DOCUMENTS
JP 62114921 5/1987

OTHER PUBLICATIONS

Beletskaya et al: "First Example of Catalytic Sandmeyer Reaction" XVI. Fechem Conference on Organometallic Chemistry, [Online], Sep. 3, 2005 (Sep. 8, 2005), p. P172, XP002463451, Budapest Hungary Retrieved from the Internet: URL:http://comc16.chem.elte.hu/pdffiles/Posters/Poster171_180.pdf> retrieved on Dec. 3, 2007 & Beletskaya et al: "Catalytic Sandmeyer Bromination" Synthesis, No. 16, Jul. 12, 2007, pp. 2534-2538, XP002463452.
Doyle et al: "Alkyl Nitrite-Metal Halide Deamination Reactions, 2. Substitutive Deamination of Arylamines by Alkyl Nitrites and Copper (II) Halides. A Direct and Remarkably Efficient Converstion of Arylamines to Aryl Halides", J. Or. Chem., vol. 42, No. 14, 1977, pp. 2426-2431.

*Primary Examiner* — Jafar Parsa
(74) *Attorney, Agent, or Firm* — Rebecca Howard

(57) ABSTRACT

The present invention relates to a process for the production of compounds of formula (I) wherein X is fluoro, chloro, bromo or iodo and n is 1, 2, 3 or 4, which process comprises reacting a compound of formula (II) wherein the substituents are as defined for formula (I), with inorganic nitrite in an acidic aqueous medium in the presence of bromide and a copper catalyst and wherein the process is carried out as a one-pot reaction.

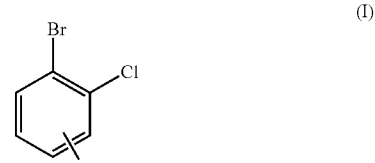

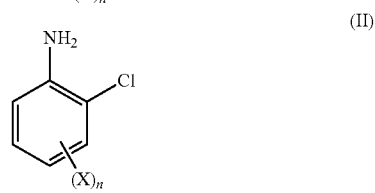

12 Claims, No Drawings

PROCESS FOR THE PRODUCTION OF SUBSTITUTED BROMOBENZENES

This application is a 371 of International Application No. PCT/EP2007/008697 filed Oct. 8, 2007, which claims priority to EP 06022279.1, filed Oct. 25, 2006, the contents of which are incorporated herein by reference.

The present invention relates to a process for the production of substituted ortho-chloro-bromobenzenes useful as intermediates in the production of agrochemicals, such as fungicides and/or herbicides.

1-Bromo-2,3-dichloro-benzene and 2-bromo-1,3-dichloro-benzene are valuable intermediates in the preparation of benzonorbornene fungicides, such as 3-difluoromethyl-1-methyl-1H-pyrazole-4-carboxylic acid (9-isopropyp-1,2,3,4-tetrahydro-1,4-methano-naphthalen-5-yl)-amide, a fungicide described in WO 04/35589 and WO 06/37632. 9-Isopropyl-1,2,3,4-tetrahydro-1,4-methano-naphthalen-5-ylamine can be produced from 1-bromo-2,3-dichloro-benzene or 2-bromo-1,3-dichloro-benzene as described in EPA 05027072.7 in examples 2b, 2d, 5 and 6b. 9-Isopropyl-1,2,3,4-tetrahydro-1,4-methano-naphthalen-5-ylamine can be used for the production of 3-difluoromethyl-1-methyl-1H-pyrazole-4-carboxylic acid (9-isopropyp-1,2,3,4-tetrahydro-1,4-methano-naphthalen-5-yl)-amide by amidation of 3-difluoromethyl-1-methyl-1H-pyrazole-4-carboxylic acid as described in WO 04/35589.

Bromo-2-chloro-4-fluoro-benzene is a valuable intermediate in the preparation of herbicides as described in JP-6-2114-921.

Agrochemicals are generally produced in large quantities. For example the fungicide chlorothalonil was produced in 2005 in a quantity of over 23,000 metric tons and the herbicide atrazine in a quantity of over 68,000 metric tons.

Several methods of preparing substituted ortho-chloro-bromobenzenes have been published. Said compounds can be prepared by the so-called Sandmeyer reaction in which an amino group is substituted by bromine via a diazonium salt (as described in Recueil des Travaux Chimiques des Pays-Bas et de la Belgique, 1932, 51, 98-113; JP-6-2114-921 and Journal of Organic Chemistry (1977), 42(14), 2426-31) or by direct aromatic bromination in which a hydrogen atom is substituted by bromine (as described in Recueil des Travaux Chimiques des Pays-Bas, 1962, 81, 365-379).

The Sandmeyer reaction for the preparation of substituted ortho-chloro-bromobenzenes involves a two step process: conversion of an aniline into a diazonium salt (diazotation) followed by replacement of the diazo group by bromine (bromination). The outcome of this reaction however strongly depends on the position and nature of the additional substituents on the aromatic ring giving poor to very good yields.

Diazotation of substituted ortho-chloro-anilines is usually carried out in acidic aqueous reaction media at temperatures around 0° C. using inorganic nitrite to quantitatively form the diazonium salts as intermediates. The resulting cold reaction mixture is slowly added to an aqueous solution containing high concentrations of cuprous bromide. Said method is described in Recueil des Travaux Chimiques des Pays-Bas et de la Belgique, 1932, 51, 98-113 and JP-6-2114-921. In both examples an equimolar amount of cuprous bromide is used. Although good yields of the desired substituted ortho-chloro-bromobenzenes are achieved, said method has significant drawbacks making it less suitable for large-scale production. First, two reaction vessels are needed: one for the diazotation step and a second one for the bromination step, this significantly increases the production costs. Second, the need for equimolar amounts of expensive cuprous bromide as well as the large-scale disposal of aqueous copper waste significantly increases the production costs. Third, this reaction scheme generally has a low throughput due to the fact that the diazotation generally has to be carried out under dilute conditions. Furthermore, in many cases the resulting diazonium salts are of low solubility in the aqueous medium. Hence, the handling of residual diazonium salt solid in the diazotation vessel after the diazotation step is a challenging task.

A reversed addition scheme, i.e. adding an acidic cuprous bromide solution to the diazonium salt mixture is not well suited for large-scale production because of heat generation and gas formation, which are both difficult to control.

A modified Sandmeyer reaction has been developed which leads to a more simplified reaction procedure. Unlike the above method, requiring inorganic nitrite in an acidic aqueous reaction media to produce the diazonium salt, an organic nitrite ester, such as tert-butyl nitrite or iso-pentyl nitrite, in an organic solvent can be used as a mild in situ diazotizing agent. Said reaction is carried out as a one-pot reaction using cuprous bromide as brominating agent and is described by Doyle et al in Journal of Organic Chemistry (1977), 42(14), 2426-31. Although in the method as described by Doyle et al the diazotation step and the bromination step can be performed within one vessel, again an equimolar amount of cuprous bromide is needed, leading to the above-mentioned drawbacks. Furthermore in the method as described by Doyle et al 1.5 equivalents of the organic nitrite ester are used; in large-scale production, this high amount of organic nitrite ester raises safety concerns and adds to the complexity of organic solvent recovery, leading to higher production costs.

Also direct aromatic bromination is not well suited for large-scale production of substituted ortho-chloro-bromobenzenes. By using this method, other isomers are formed as undesired impurities. When 1-bromo-2,3-dichloro-benzene is produced from ortho-dichloro-benzene as described in Recueil des Travaux Chimiques des Pays-Bas, 1962, 81, 365-379, the main isomer formed is the undesired 1-bromo-3,4-dichloro-benzene; the desired product 1-bromo-2,3-dichloro-benzene is formed only in 7% of the reaction products.

The aim of the present invention is therefore to provide a novel process for the production of substituted ortho-chloro-bromobenzenes that avoids the disadvantages of the known processes mentioned above and makes it possible to prepare those compounds in high yields and good quality in an economically advantageous and easily handled way.

The present invention accordingly relates to a process for the production of compounds of formula I

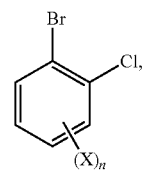

wherein X is fluoro, chloro, bromo or iodo and n is 1, 2, 3 or 4, which process comprises reacting a compound of formula II

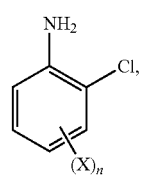

wherein the substituents are as defined for formula I, with inorganic nitrite in an acidic aqueous medium in the presence of bromide and a copper catalyst and wherein the process is carried out as a one-pot reaction.

The process according to the invention is suitable preferably for the production of compounds of formula I wherein X is chloro. The process according to the invention is suitable preferably for the production of compounds of formula I wherein n is 1 or 2, more preferably 1. The process according to the invention is especially suitable for the preparation of compounds of formula I wherein X is chloro and n is 1. The process according to the invention is especially suitable for the preparation of 1-bromo-2,3-dichloro-benzene or 2-bromo-1,3-dichloro-benzene.

Suitable inorganic nitrites for the process of the instant invention are alkali nitrites, for example sodium nitrite or potassium nitrite, earth alkali nitrites, for example magnesium nitrite or calcium nitrite or mixtures thereof. Preferred inorganic nitrites are alkali nitrites, most preferred inorganic nitrite is sodium nitrite.

Suitable amounts of inorganic nitrite for the process of the instant invention are, for example, from 1 to 3 equivalents, preferably from 1.0 to 1.5 equivalents, especially from 1.0 to 1.2 equivalents.

Suitable sources for bromide are hydrobromic acid, inorganic bromides or mixtures thereof. Suitable inorganic bromides are alkali bromides, for example sodium bromide or potassium bromide, or earth alkali bromides, for example magnesium bromide or calcium bromide; preferred inorganic bromides are alkali bromides, most preferred inorganic bromide is sodium bromide.

Suitable total amounts of bromide for the process of the instant invention are, for example, from 2.5 to 8 equivalents, preferably from 3 to 6 equivalents, especially from 3 to 5 equivalents.

Suitable copper catalysts are copper-(I)-ions, copper-(II)-ions, metallic copper or mixtures thereof. Suitable sources for copper-(I)-ions are copper-(I)-bromide or copper-(I)-oxide; preferred is copper-(I)-bromide. Suitable sources for copper-(II)-ions are copper-(II)-bromide, copper-(II)-sulfate or copper-(II)-oxide; preferred is copper-(II)-bromide or copper-(II)-sulfate. A suitable source of metallic copper is copper powder.

In one embodiment of the invention copper-(I)-ions and/or copper-(II)-ions are used as the copper catalyst.

In another embodiment of the invention copper-(I)-ions are used as copper catalyst.

In another embodiment of the invention copper-(II)-ions are used as copper catalyst.

In yet another embodiment of the invention metallic copper is used as copper catalyst.

Suitable amounts of copper catalysts are, for example, from 0.01 to 2 equivalents, preferably from 0.05 to 1 equivalent, more preferably from 0.05 to 0.5 equivalents, even more preferably from 0.05 to 0.2 equivalents, especially from 0.05 to 0.1 equivalents. The more preferred embodiment of the invention, wherein from 0.05 to 0.2 equivalents of copper catalyst is used is especially advantageous for large-scale production as only low amounts of copper salt waste are produced.

According to the invention, an "aqueous medium" means preferably a liquid reaction medium, wherein the main component of the medium is water. The educts, products, reactants or intermediates can be dissolved, suspended or emulgated in said aqueous medium.

Suitable acids for use with the process according to the instant invention are inorganic acids, wherein the anion is either bromine or an inert anion, such as hydrobromic acid or sulphuric acid, organic acids, such as actetic acid or mixtures thereof. Preferred acid is hydrobromic acid.

Suitable amounts of acid for the process of the instant invention are, for example, from 1.5 to 5 equivalents, preferably from 1.5 to 4.0 equivalents, especially from 2.6 to 4.0 equivalents.

The process according to the invention is preferably carried out in a temperature range of from 10° C. to 100° C., more preferably in a temperature range of from 30° C. to 100° C., even more preferably in a temperature range of from 30° C. to 100° C., most preferably in a temperature range of from 35° C. to 65° C.

In one embodiment of the invention, after formation of the reaction product, the reaction mixture is heated above the melting point of the reaction product. This embodiment of the invention can be used for the preparation of 1-bromo-2,3-dichloro-benzene, which has a melting point of around 60° C. By heating the reaction mixture after formation of 1-bromo-2,3-dichloro-benzene to 65° C., the initial solid product in the aqueous reaction suspension is transformed into a molten liquid, which can be easily isolated by phase separation.

The skilled man will recognize that the desired substituted benzene product may be extracted from the aqueous reaction suspension by addition of a suitable water-immiscible aromatic organic solvent such as Toluene, or halogenated aliphatic solvent such as methylenechloride or chloroform or aliphatic organic solvent—in particular a (cyclo) aliphatic hydrocarbon such as hexane or cycyclohexane. The organic phase may then be recovered from the reaction mixture by phase separation and the product may then be isolated by distilling off the organic solvent.

The reaction time for the process according to the instant invention is preferably from 1 to 24 hours, more preferably from 2 to 16 hours, even more preferably from 2 to 5 hours.

According to the invention "one-pot reaction" means that the process of diazotation and bromination according to the invention is performed without change of the reaction vessel. In one embodiment of the invention, the work-up of the reaction product is carried out in an additional vessel, for example a vessel suitable for vacuum distillation in the case that the reaction product is purified via vacuum distillation.

The addition of the inorganic nitrite to the compound of formula II in an acidic aqueous medium in the presence of the bromide and the copper catalyst has the consequence that the aryldiazonium intermediate is short-lived and reacts in situ to produce the compound of formula I in the same reaction vessel without isolation of the aryldiazonium intermediate.

In one embodiment of the invention, the inorganic nitrite is added to a mixture of the compound of formula II, bromide and copper catalyst in the acidic aqueous medium. In particular in this embodiment, in said mixture, the compound of formula II, the bromide and the copper catalyst are present in their total amounts to be used for the process according to the invention.

In respect of this embodiment, it is particularly preferred that the inorganic nitrite is added in the form of an aqueous solution.

In another embodiment of the invention, the inorganic nitrite is added to a mixture of the compound of formula II in an acidic aqueous medium in the form of a mixture comprising the inorganic nitrite, the bromide and the copper catalyst.

In yet another embodiment of the invention, the inorganic nitrite is added to a mixture of the compound of formula II and the bromide in an acidic aqueous medium in the form of a mixture comprising the inorganic nitrite and the copper catalyst.

In yet another embodiment of the invention, the inorganic nitrite is added to a mixture of the compound of formula II and the copper catalyst in an acidic aqueous medium in the form of a mixture comprising the inorganic nitrite and the bromide.

The compounds of formula II are known or can be prepared analogously to processes known in the art.

The present invention is illustrated with the aid of the following Examples.

EXAMPLE P1

Preparation of 1-bromo-2,3-dichlorobenzene
(compound A1)

32.7 g 2,3-Dichloroaniline (0.20 mole) is added to a mixture of 21.4 g of NaBr (0.20 mole, 1.0 equivalent), 110.0 g of 48% aqueous HBr (0.66 mole, 3.3 equivalents) and 70 ml water at 30-45° C. The mixture is stirred for 15 minutes at 30-45° C. and then heated to 60° C. Then 2.9 g Cu(I)Br (0.02 mole, 0.10 equivalent) is added and the mixture is stirred for 15 minutes at 60° C. After this, an aqueous solution of NaNO$_2$ (40% solution in water, 37.6 g, 0.22 mole, 1.1 equivalents) is added via subsurface feeding over a period of 2 hours at 60-65° C. The reaction mixture is stirred for 30 minutes at 60-65° C. The organic phase containing the reaction product is separated from the aqueous phase and is cooled to ambient temperature, leading to solidification of the reaction product. The remaining liquid is discarded and the crude product is washed two times with 10 ml water and dried under vacuum. 44.0 g (89% of theory) of 1-bromo-2,3-dichlorobenzene is obtained in the form of a light brown solid (purity: 91%). For further characterisation, the crude product was purified by vacuum distillation (130° C./20 mmHg). 38.0 g (84% of theory) of pure 1-bromo-2,3-dichlorobenzene is obtained in the form of white crystals.

EXAMPLE P2

Preparation of 1-bromo-2,3-dichlorobenzene
(compound A1)

32.7 g 2,3-Dichloroaniline (0.20 mole) is added to a mixture of 168.5 g of 48% aqueous HBr (1.0 mole, 5.0 equivalents) and 40 ml water at 30-40° C. The mixture is stirred for 15 minutes at 30-40° C. and then heated to 45° C. Then 2.9 g Cu(I)Br (0.02 mole, 0.10 equivalent) is added and the mixture is stirred for 15 minutes at 45° C. After this, an aqueous solution of NaNO$_2$ (40% solution in water, 35.6 g, 0.21 mole, 1.0 equivalents) is added via subsurface feeding over a period of 2 hours at 45° C. The reaction mixture is stirred for 30 minutes at 45° C. After this, the reaction mixture is heated to 60-65° C. The organic phase containing the reaction product is separated from the aqueous phase and is cooled to ambient temperature, leading to solidification of the reaction product. The remaining liquid is discarded and the crude product is washed twice with 10 ml water and dried under vacuum. 40.0 g (80% of theory) of 1-bromo-2,3-dichlorobenzene is obtained in the form of a light brown solid (purity: 90%).

EXAMPLE P3

Preparation of 1-bromo-2,3-dichlorobenzene
(compound A1)

32.7 g 2,3-Dichloroaniline (0.20 mole) is added to a mixture of 21.4 g of NaBr (0.20 mole, 1.0 equivalent), 110.0 g of 48% aqueous HBr (0.66 mole, 3.3 equivalents) and 70 ml water at 30-40° C. The mixture is stirred for 15 minutes at 30-40° C. and then heated to 45° C. Then 5.1 g CuSO$_4$*5H$_2$O (0.02 mole, 0.10 equivalent) is added and the mixture is stirred for 15 minutes at 45° C. After this, an aqueous solution of NaNO$_2$ (40% solution in water, 37.6 g, 0.22 mole, 1.1 equivalents) is added via subsurface feeding over a period of 2 hours at 45° C. The reaction mixture is stirred for 30 minutes at 45° C. After this, the reaction mixture is heated to 60-65° C. The organic phase containing the reaction product is separated from the aqueous phase and is cooled to ambient temperature, leading to solidification of the reaction product. The remaining liquid is discarded and the crude product is washed twice with 10 ml water and dried under vacuum. 44.0 g (83% of theory) of 1-bromo-2,3-dichlorobenzene is obtained in the form of a light brown solid (purity: 85%).

EXAMPLE P4

Preparation of 1-bromo-2,3-dichlorobenzene
(compound A1)

163 g 2,3-Dichloroaniline (1.0 mol) is added to a mixture of 3250 g of 30% aqueous HBr (12.0 mole) and 25.4 g copper powder of a particle size of approx. 45μ at 35-37° C. The mixture is stirred for 15 minutes at 35-37° C. Then, 766 g of an aqueous solution of NaNO$_2$ (40% solution in water, 4.44 mole) is added via subsurface feeding over a period of 3 hours at 35° C. Parallel to the addition of the sodium nitrite 489 g 2,3-dichloroaniline (3.0 mol) is added over a period of 2.5 hours at the same temperature. The addition of dichloraniline starts 15 minutes after the start of the addition of sodium nitrite. After all additions are complete the reaction mixture is stirred for 30 minutes at 35° C. Then, the reaction mixture is heated to 60-65° C. The organic phase containing the reaction product is separated from the aqueous phase. The remaining liquid is discarded and the crude product is washed twice with 200 ml water. 792.2 g of crude solid 1-bromo-2,3-dichlorobenzene is obtained (87.7% of theory) with a purity of 86.2%).

The following compounds of formula I can be prepared on the basis of the above Examples:

TABLE 1

Compounds of formula I

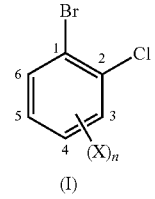

(I)

| Comp. No. | (X)$_n$ |
|---|---|
| A1 | 3-Cl |
| A2 | 6-Cl |
| A3 | 3-F |
| A4 | 6-F |
| A5 | 4-F |
| A6 | 4-Cl |
| A7 | 4,6-di-Cl |
| A8 | 4,6-di-F |

The present invention makes it possible to produce substituted ortho-chloro-bromobenzenes in a controlled manner in a high yield, with a high degree of regioselectivity and at low cost.

The present invention makes it possible to produce substituted ortho-chloro-bromobenzenes without the use of an organic solvent, if desired.

The starting materials for the process of the present invention are distinguished by ready accessibility and ease of handling and are also inexpensive.

What is claimed is:

1. A process for the production of compounds of formula I

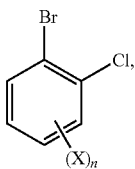
(I)

wherein X is fluoro, chloro, bromo or iodo and n is 1, 2, 3 or 4, which process comprises reacting a compound of formula II

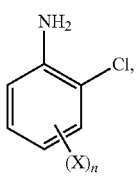
(II)

wherein the substituents are as defined for formula I, with inorganic nitrite in an acidic aqueous medium in the presence of bromide and a copper catalyst and wherein the process is carried out as a one-pot reaction.

2. A process according to claim 1, wherein X is chlorine.

3. A process according to claim 1, wherein n is 1.

4. A process according to claim 1, wherein the compound of formula I is 1-bromo-2,3-dichloro-benzene or 2-bromo-1,3-dichloro-benzene.

5. A process according to claim 4, wherein the compound of formula I is 1-bromo-2,3-dichloro-benzene.

6. A process according to claim 1, wherein from 0.01 to 2 equivalents of copper catalyst is used.

7. A process according to claim 1, wherein copper-(I)-ions and/or copper-(II)-ions are used as copper catalyst.

8. A process according to claim 1, wherein the copper catalyst is finely divided metallic copper.

9. A process according to claim 1, wherein the process is carried out at a temperature range of from 10° C. to 100° C.

10. A process according to claim 1, wherein the inorganic nitrite is added to a mixture of the compound of formula II, bromide and copper catalyst in the acidic aqueous medium.

11. A process according to claim 1, wherein the inorganic nitrite is added in the form of an aqueous solution.

12. A process according to claim 1, wherein the organic solvent soluble substituted benzene product of formula I is recovered from the aqueous reaction phase by addition to it of a suitable organic solvent followed by phase separation.

* * * * *